United States Patent [19]

Rowsey et al.

[11] 4,156,840

[45] May 29, 1979

[54] THERMOELECTRIC METAL SORTER

[75] Inventors: James H. Rowsey, Huntington, W. Va.; Charles E. Snavely, Proctorville, Ohio; Clayton D. Luce, Huntington, W. Va.

[73] Assignee: Huntington Alloys, Inc., Huntington, W. Va.

[21] Appl. No.: 916,703

[22] Filed: Jun. 19, 1978

[51] Int. Cl.² .................... G01R 5/28; G01N 25/00
[52] U.S. Cl. .................................. 324/32; 73/15 R
[58] Field of Search .................... 73/15 R; 324/32

[56] References Cited

U.S. PATENT DOCUMENTS

| | | | |
|---|---|---|---|
| 3,093,791 | 6/1963 | Richards | 73/15 R |
| 3,667,032 | 5/1972 | Summers | 324/32 |
| 3,737,762 | 6/1973 | Fletcher et al. | 324/32 |

*Primary Examiner*—Donald O. Woodiel
*Attorney, Agent, or Firm*—Lewis Messulam; Ewan C. MacQueen

[57] ABSTRACT

A metal sorter including a pair of electrically conductive probes of identical metallic composition are placed in contact with a metallic specimen. A thermoelectric heat pump is positioned between the two probes to produce a temperature difference therebetween, a temperature sensing device senses the temperature difference and provides an electric signal to control the electric power supplied to the heat pump. A detection device provides an electric signal indicative of the potential difference between the probes.

9 Claims, 4 Drawing Figures

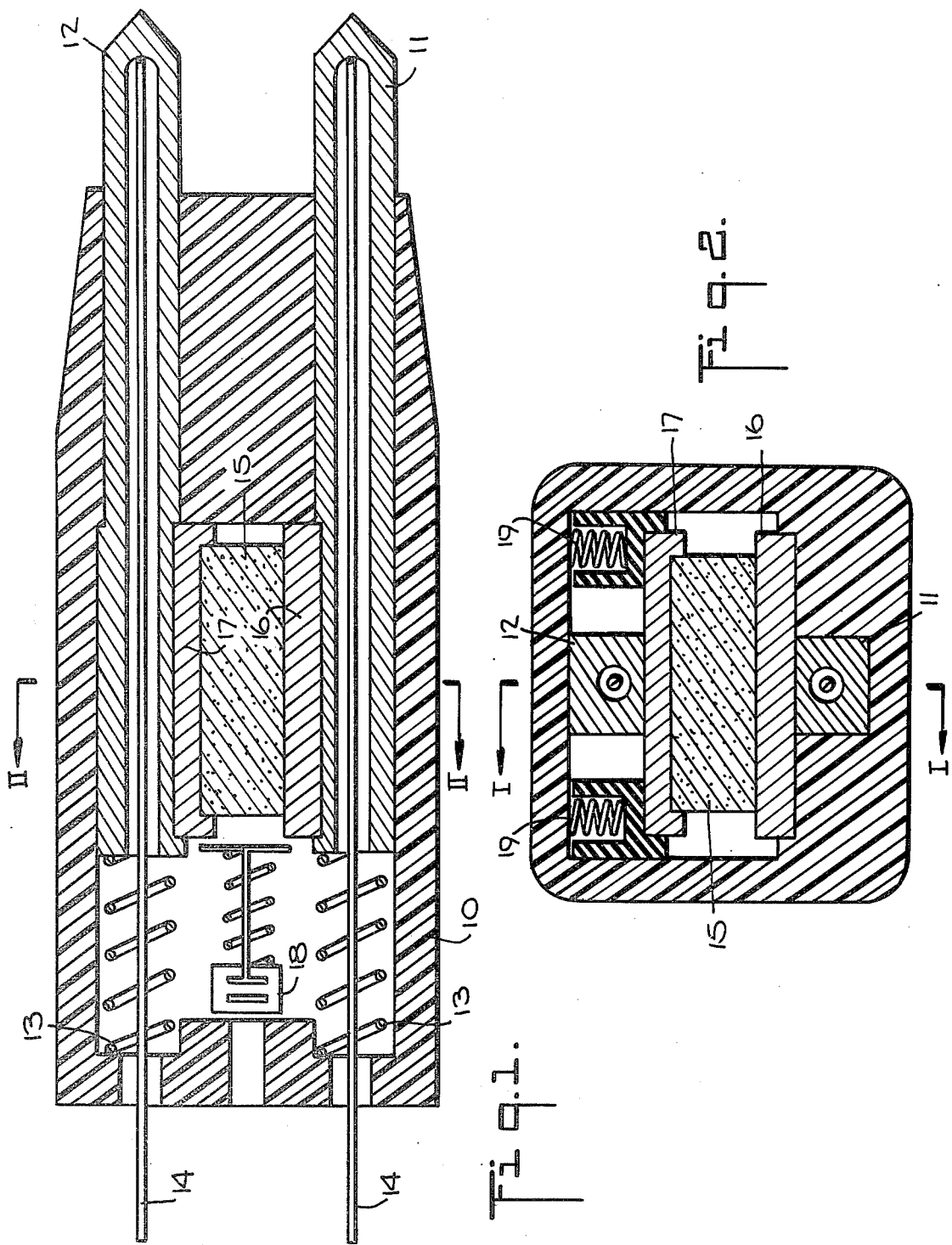

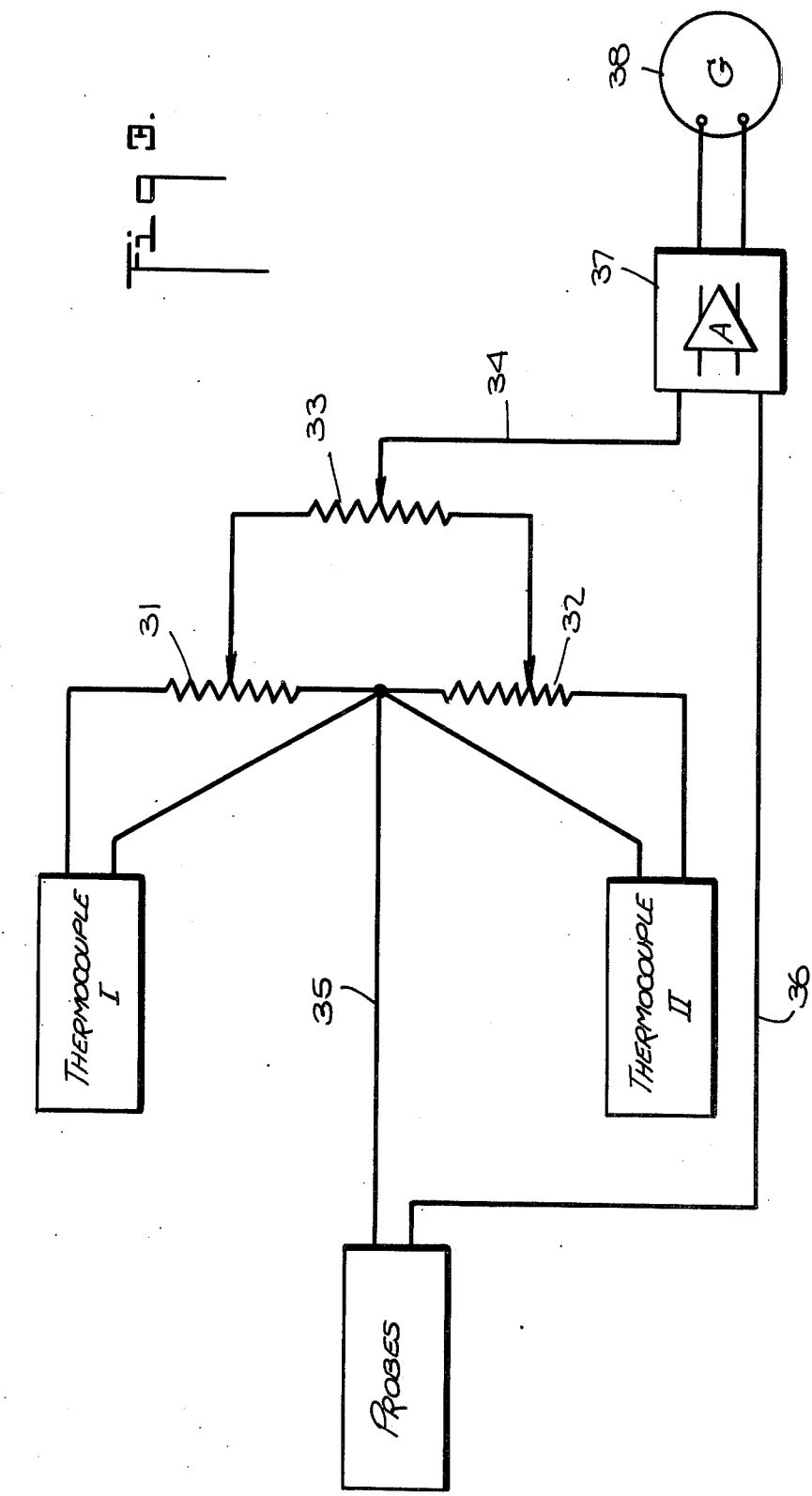

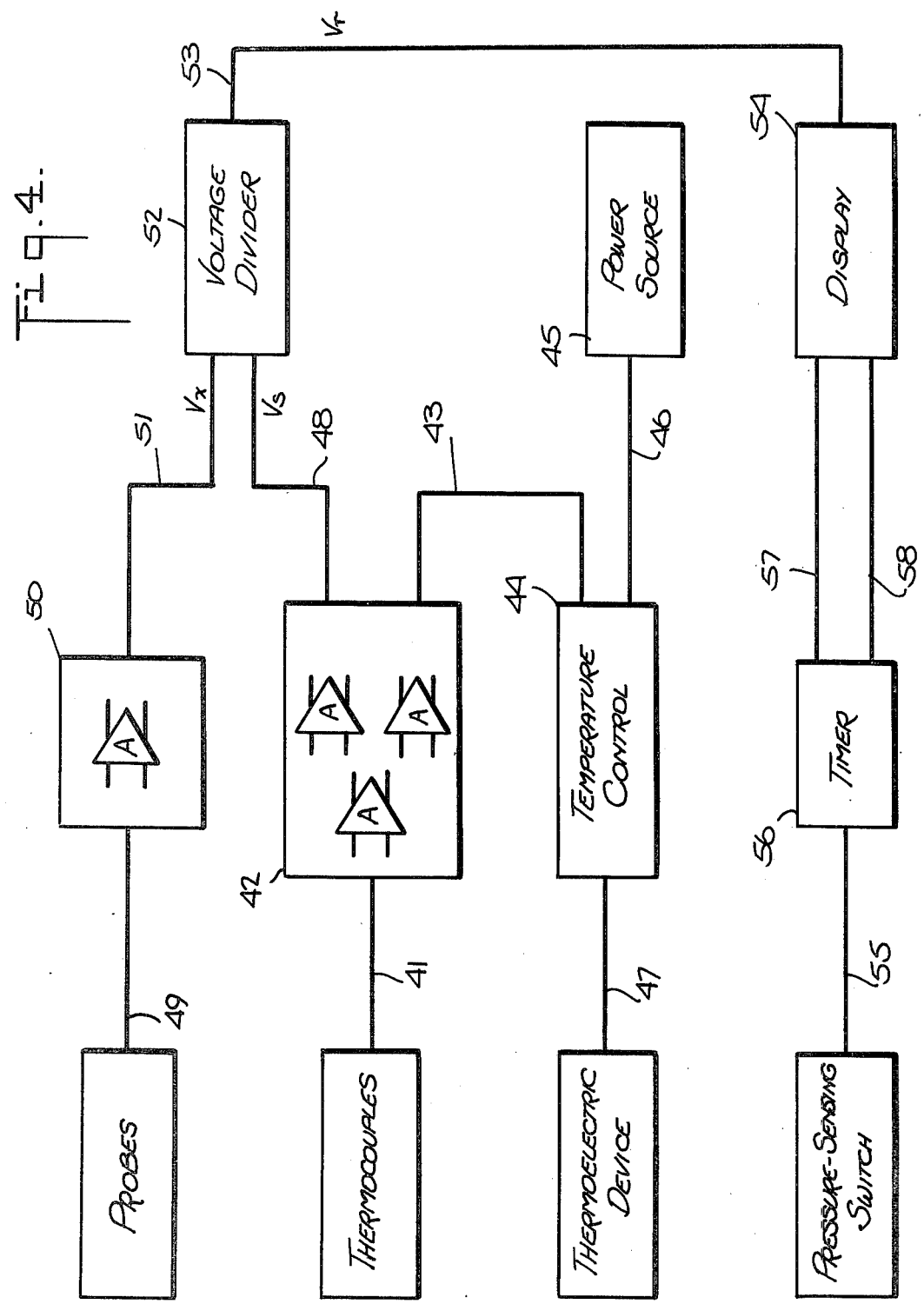

THERMOELECTRIC METAL SORTER

FIELD OF THE INVENTION

The present invention relates to metal-sorting devices, and in particular to apparatus for identifying a metallic specimen by means of the electro-motive force generated between a pair of electrically conductive probes at different temperatures from one another when they are contacted with the specimen to be identified.

BACKGROUND OF THE INVENTION

The need has long existed for a device whereby both manufacturers and end users of a variety of alloys could conveniently identify metallic samples from which, for one reason or another, conventional identification markings are absent. Non-destructive testing methods which have been resorted to for such sorting purposes have relied on one or more of various physical characteristics of the metallic samples, including thermal properties, magnetic properties electrical properties, triboelectric properties, and thermoelectric properties. In the case of thermoelectric testing, use is made of the Seebeck effect whereby an electro-motive force (emf) is generated between two junctions of a dissimilar pair of metals when the junctions are at different temperatures.

One form of device for identifying metals by reliance on their Seebeck effect is described in U.S. Pat. No. 3,667,032. The device in questions features a pair of probes which are made of identical electrically conductive material. One of the probes is electrically heated to produce a predetermined temperature difference between the probes, and the emf between the hot and cold probes is measured. The use of probes made of the same material as one another eliminates the need to know precisely what the temperature of each probe is. However, it remains essential to know what the temperature difference between the probes is, with some accuracy, if the measured emf is to be relied upon for identification of the unknown metal.

An improvement on this technique which has been used by the assignee of the present invention for many years avoids the need for maintaining a precise temperature difference between the probes. This is achieved by relying not simply on the absolute value of the emf generated between the probes and the unknown sample, but on the relationship between that emf (which we will designate $E_x$) and an electrical signal which is indicative of the temperature difference between the probes. This temperature indicating signal (which we will designate $E_s$) can be derived for example from one or more thermocouples attached to the probe tips. Any change in the temperature difference between the probes will result in variations of both $E_x$ and $E_s$. While in general the dependence of $E_x$ and $E_s$ on the temperature difference will not be identical, the difference in behavior can be ignored for minor changes in the temperature difference. Thus the ratio of $E_s$ to $E_x$ will be substantially constant despite minor variations in the temperature difference between the probes. In practice a potentiometric bridge circuit has been used to determine the above mentioned ratio obtained when a particular probe assembly is contacted with a series of known metals or alloys, and a chart was thereby constructed which enabled metallic specimens to be identified by means of the $E_s$ to $E_x$ ratio determined when the same probe assembly was contacted with the unknown specimen.

However, while the Seebeck effect measurement has proved a useful tool for metal sorting, and has indeed been used for this purpose by the assignee for many years, it has not been possible until now to design a reliable metal sorter having the desired degree of portability. Thus, whereas many devices are described in the literature as being portable, they are in fact cumbersome devices, requiring to be connected to a mains electrical supply or to some bulky power unit. In the known thermoelectric metal sorters, the probe head itself tends to be bulky because of the need to keep a substantial distance between the two probes in order to avoid the resistance heater surrounding the hot probe from also heating the cold probe. Other problems encountered in using such sorters arise from the need to establish good electrical and thermal contact between the probes and the unknown sample during the test. This requires the application of pressure to urge both probes against the sample, and the maintaining of such pressure while balancing a potentiometer or while reading a meter which may be fluctuating with the pressure applied to the probe head.

OBJECTS OF THE INVENTION

It is an object of the present invention to provide an improvement in the method of sorting metals by relying on the Seebeck effect exhibited by them, which improvement can be embodied in a device small enough to be hand-held and used without connection to any external power supply.

It is a further object of the invention to provide such an improved metal sorting device, the design of which facilitates the establishment of good electrical and thermal contact between the probes and a sample to be tested.

SUMMARY OF THE INVENTION

The present invention provides a metal sorter comprising a pair of electrically conductive probes of identical metallic composition, means for producing a temperature difference between said probes, sensing means for providing a first electrical signal indicative of said temperature difference, and detection means for detecting a second electrical signal indicative of the potential difference between said probes when said probes are contacted, in operation, with a metallic specimen to be identified and providing an indication of the ratio of said signals, wherein said means for providing said temperature difference comprises a thermoelectric heat pump effective to pump heat between a pair of opposed faces thereof in response to electrical power supplied thereto, said heat pump being mounted between said probes such that each of said probes is maintained in thermal contact with a respective one of said opposed faces, and means responsive to said first signal for supplying electrical power to said heat pump so as to maintain said first signal substantially at a predetermined operating level.

The "thermoelectric heat pump" referred to in the present specification and claims in a well-known device which makes use of the Peltier effect whereby the application of a potential difference across a junction of dissimilar metals produces a temperature difference across the junction. Such devices are commercially available in the form of small plate-shaped bodies capable of producing a temperature difference of the order of 50° C. between opposed flat faces which are only about 0.5 cm apart. In operation, such a device acts as a pump transferring heat from an object in contact with one of its faces to an object in contact with the opposite face so that the first object is cooled while the second is heated. The use of such a heat pump in the metal sorter of the invention is essential to the success of the invention in enabling the probes to be closely spaced and hence enabling the overall metal sorter to be made more compact. Thus in known devices which employ resistance heating of one or both of the probes, the colder probe is either heated to a lesser extent than the hotter probe, or else maintained at ambient temperature. With such an arrangement, the ability to maintain a desired temperature difference between the probes is predicated on the thermal shielding of the probes from one another. In contrast, the use of a heat pump results in actual cooling of the cold probe, and the maintaining of a desired temperature difference between the probes is predicated on the heat pumping efficiency of the thermoelectric device.

In a preferred embodiment of the invention a housing is provided which is made of electrically insulating material of low thermal conductivity and which encases the whole of the metal sorter including the required source of electrical power. In this embodiment, each of the probes is in the shape of an elongate body mounted in the housing so that only the tip thereof protrudes from the housing. The probe has a bore in which a thermocouple is positioned to sense the temperature near the tip which protrudes from the housing. The probes are mounted parallel to one another within the housing and are slideable over a small distance relative to one another so as to vary the extent to which each probe protrudes from the housing. The probe assembly is spring-loaded in two mutually perpendicular directions. Firstly, a set of springs urge each of the probes towards its position of maximum protrusion. A second set of springs urges the probes transversly to their axial direction and towards one another so as to ensure good thermal contact between each probe and a respective face of a heat pump positioned between the probes.

The ratio between the temperature sensing signal and the signal produced by the probes when they contact the unknown specimen can be determined by balancing these signals against one another using a standard potentiometric circuit. Alternatively, in accordance with a further preferred feature of the invention, the first and second signals are amplified and then fed to a voltage divider which produces a third signal proportional to the ratio of the first and second signals to one another. This third signal can then be fed to a voltmeter, the read-out of which can be used to identify the unknown specimen.

Yet another preferred feature of metal sorters in accordance with the invention, is the provision of means for controlling the operation of the voltmeter used to display the metal identification signal so as to avoid the need for having to read that meter while contacting the unknown specimen at the same time, and also to obviate the difficulties involved in reading a meter which might be fluctuating slightly. The control means used involves a position sensing switch, which senses a predetermined displacement of both of the probes when the probe assembly is urged into contact with a specimen, and energizes a timing device which outputs two control signals sequentially to the display voltmeter. The first of these control signals enables the voltmeter to display the voltage resulting from the voltage dividing circuit. The second control signal renders the voltmeter insensitive to changes in the voltage divider output so that the voltmeter read-out is held constant until these control signals are discontinued. The timing device continues to emit these first and second control signals for as long as it is energized by operation of the position sensing switch, and for a predetermined period after it is de-energized. If pressure on the probe tips is released and immediately re-applied, the re-energizing of the timing device will cause the control signals already emitted to be discontinued, and after a finite delay, a new pair of control signals are emitted. As a result, a new read-out is displayed and held by the voltmeter.

BRIEF DESCRIPTION OF THE DRAWINGS

The invention will now be specifically described with reference to preferred embodiments thereof as illustrated in the accompanying drawings in which:

FIGS. 1 and 2 schematically represent mutually perpendicular cross-sections of the probe assembly in a preferred embodiment of the invention;

FIG. 3 represents a circuit which can be used for comparing the emf generated by an unknown specimen with the voltage obtained from the sensing thermocouples in a sorter according to the invention; and FIG. 4 represents the electrical circuit used in the preferred embodiment of FIGS. 1 and 2.

DETAILED DESCRIPTION OF THE EMBODIMENTS

Referring to FIGS. 1 and 2 a preferred probe assembly is shown in mutually perpendicular cross-sectional views, so that FIG. 1 is a cross-section through the line I—I of FIG. 2, while FIG. 2 is a section through the line II—II of FIG. 1. The assembly has a housing 10 made of an electrically insulating material such as a plastic having low thermal conductivity. Within this housing are a pair of probes 11 and 12, each of which is slideable longitudinally independently of the other probe. Each probe is of rectangular or square cross-section for a substantial portion of its length, and of circular cross-section for the remainder of its length, the cylindrical portion terminating in a pointed tip which protrudes from the housing and contacts an unknown specimen in operation. For convenience, the probe need not be of unitary construction, but may be provided with a detachable tip which can be replaced in the event of wear.

Each probe is provided with a spring 13 which, acting on the probe end remote from its pointed tip, urges the probe to its position of maximum protrusion from the housing. Each probe is provided with a bore through which a thermocouple 14 passes to measure the probe temperature in the vicinity of the tip. While the thermocouples used in the two probes may be identical to one another, this is by no means essential and indeed where a potentiometric bridge is used as hereinafter described, it may be preferred to employ thermocouples which are different from one another.

A thermoelectric heat pump 15 is positioned between the probes and a pair of metallic blocks 16 and 17 are sandwiched between a respective probe and a respective face of the heat pump. The block 16 is keyed into a face of the probe 11 so that the probe 11 and the block 16 slide together as a unit. The heat pump is keyed into a face of the block 17 while the latter is keyed on the opposite face to a face of the probe 12. As a result, the combination of heat pump 15, block 17 and probe 12 can slide as a single unit with respect to the housing and with respect to the combination of block 16 and probe 11. A switch 18 is positioned rearwardly of the probes so that it will be activated when the probes have been retracted to a predetermined extent. A second set of springs 19 (shown in FIG. 2) acts to urge the probes towards one another and thus enables good thermal conductivity to be maintained throughout the sliding displacement of the probes between the heat pump and probes through the respective spacing blocks 16 and 17.

In using the sorter, power is applied to the heat pump to provide a temperature difference between the probes 11 and 12. By using a signal derived from the thermocouples 14 to control the power input to the heat pump, a predetermined temperature difference can be produced. When this has been accomplished, the test of an unknown sample is performed by urging the probe tips onto the surface of the sample with enough pressure to cause the probes to retract against the resistance of the springs 13. Activation of the switch 18 indicates that sufficient pressure has been applied between the probe tips and the unknown specimen to ensure the desired electrical and thermal contact for a reliable measurement to be made. The activation of the switch is made to render operable the comparison circuit used to determine the ratio of the emf present between the probes to a voltage derived from the thermocouples 14.

FIG. 3 shows a circuit which can be used to determine potentiometrically the voltage ratio from which the unknown specimen can be identified. The thermocouples inserted in the probes of FIG. 1 are represented as thermocouple I and thermocouple II in FIG. 3. The output from each thermocouple is fed across a respective one of a pair of potentiometers 31 and 32 connected in series and referred to herein as trimpots. Each of these trimpots supplies a voltage to a respective end of a potentiometer 33. The emf generated by the unknown specimen in contact with the probes is balanced against the voltage impressed across the potentiometer 33 in the following manner. One of the probes is connected via line 35 to the common point of the trimpots 31 and 32. The other probe is connected through lines 36 and 34 to the balancing terminal of the potentiometer 33, via an amplifier 37 and a galvanometer 38. This arrangement enables an accurate determination of the null-deflection condition at which the setting of the potentiometer 33 will provide an indication of the composition of the tested specimen. When using such a circuit arrangement, it may be advantageous to use thermocouples which differ from one another, e.g., which provide signals of different polarities. By appropriate choice of the thermocouples, and appropriate setting of the trimpots 31 and 32, the voltage difference applied across the potentiometer 33 is chosen to enable the range of the potentiometer to be suitable for the range of materials to be tested. Having adjusted the setting of the trimpots 31 and 32, the instrument can be calibrated using a variety of known metallic specimens by balancing the potentiometer 33 so as to obtain in each case a zero deflection on the galvanometer 38, and noting the setting of the potentiometer 33 for each known specimen so that an identification chart can be constructed.

While the above described potentiometric balancing method provides a reliable sorting technique, a more preferred embodiment of the invention employs circuitry which obviates the need for mechanical manipulation while contact is maintained with the specimen to be tested. This preferred alternative is illustrated in FIG. 4. For the sake of clarity, the circuit of FIG. 4 is shown and described in functional terms, and single lines are used to indicate schematically the signal path rather than specific wiring between the functional components of the circuit.

A signal representing the combined emf's produced by the temperature-sensing thermocouples is fed along the path 41 to an amplifier 42. This amplifier is in effect two amplifiers sharing a common first stage, so that it produces two outputs of different amplifications. The first amplified thermocouple signal is fed along the path 43 to a temperature controller 44. The latter is a transistorized gate which is normally in open mode to allow electrical power from a power source 45 to flow along the paths 46 and 47 to the thermoelectric heat pump between the probes. The controller is effective to cut off the power flow to the heat pump when the signal received along the path 43 exceeds a predetermined threshold operating level. In this way, the temperature difference between the probes is maintained substantially constant.

The second amplified thermocouple signal, which we shall designate $V_s$, is fed along the path 48 to a voltage-dividing circuit 52. The emf across the probes is fed along the path 49 to an amplifier 50, and the amplified probe voltage, which we shall designate $V_x$, is fed along the path 51 to the voltage-dividing circuit 52. The latter consists of a multiplier connected in negative feedback with an operational amplifier. It is effective to produce a signal $V_r$ which is proportional to the ratio of $V_x$ to $V_s$. This ratio-indicating signal $V_r$ is fed along the path 53 to a display meter 54 which is preferably a digital readout voltmeter.

Operation of the display voltmeter 54 is controlled by a timing circuit 56. This timing curcuit is energized via the path 55 by activation of the pressure-sensing switch (identified as 18 in FIG. 1) in response to retraction of the probe tips. The timing circuit is effective to generate two display-controlling signals which are fed to the display along the paths 57 and 58. These signals are respectively a DISPLAY ENABLING SIGNAL and a DISPLAY HOLDING SIGNAL. The first of these enables the digital voltmeter to display a readout indicative of the voltage $V_r$ fed to it, while the second signal "freezes" the readout of the voltmeter so that it is unaffected by subsequent changes in $V_r$. The timing sequence of these signals is as follows. The DISPLAY ENABLING SIGNAL is turned on very shortly after energization of the timing circuit. After a short delay, the DISPLAY HOLDING SIGNAL is also turned on and both control signals remain on for as long as the timing circuit remains energized and for a predetermined period thereafter unless prior to the termination of that period the timing circuit has been re-energized. This period of delay, which can be chosen to be of the order of 2 to 3 minutes, enables the display to be read after the contact has been made and broken with the specimen to be tested.

A metal sorter featuring the probe assembly illustrated in FIGS. 1 and 2 and the circuit arrangement illustrated in FIG. 4 has been constructed and tested. In this sorter the probes were made of copper, as were the conducting blocks connecting the probes to the heat pump. The latter was a commercially available ceramic module having a pumping capacity of 9 watts. The remaining components of the circuit were all commercially available units, the temperature controller, for example, included a "Darlington" transistor output stage, while the display meter was a voltmeter with a 3½-digit liquid crystal display. Power for the unit was supplied by a low voltage rechargeable battery. This was arranged to drive the heat pump through the temperature controller, and also to feed a power supply circuit which provided power to all the other functional components of the circuit.

The resulting metal sorter was a small, light-weight unit which was encased for convenience in a pistol-shaped housing which enables it to be carried in one hand.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

We claim:

1. A metal sorter comprising a pair of electrically conductive probes of identical metallic composition, means for producing a temperature difference between said probes, sensing means for providing a first electrical signal indicative of said temperature difference, and detection means for detecting a second electrical signal indicative of the potential difference between said probes when said probes are contacted, in operation, with a metallic specimen to be identified and providing an indication of the ratio of said signals, wherein said means for providing said temperature difference comprises a thermoelectric heat pump effective to pump heat between a pair of opposed faces thereof in response to electrical power supplied thereto, said heat pump being mounted between said probes such that each of said probes is maintained in thermal contact with a respective one of said opposed faces, and means responsive to said first signal for supplying electrical power to said heat pump so as to maintain said first signal substantially at a predetermined operating level.

2. A sorter according to claim 1 which is encased in a housing of electrically insulating material of low thermal conductivity, wherein said probes comprise a pair of elongate bodies mounted with their longitudinal axes parallel to one another within said housing such that only a small portion adjacent to a longitudinal extremity of each probe protrudes from said housing, said probes being slideable longitudinally over a short distance independently of one another, and wherein resilient means are provided to urge each probe towards its position of maximum protrusion from said housing.

3. A sorter according to claim 2 wherein said thermoelectric heat pump is mounted to fixed relation to one of said probes and slideable therewith relative to said other probe and to said housing, and including lateral urging means for resiliently urging said probes towards one another in a direction normal to their longitudinal axes, thereby maintaining thermal contact between said heat pump and said probes throughout sliding displacement thereof.

4. A sorter according to claim 3 wherein each probe is provided with a longitudinal bore terminating close to said extremity, and wherein said sensing means includes a thermocouple contained in said bore of each probe and in thermal contact with said extremity thereof.

5. A sorter according to claim 4 wherein said detection means comprises a potentiometric bridge circuit for comparing said first and second signals.

6. A sorter according to claim 4 wherein said detection means comprises first and second amplifier means for amplifying said first and second signals respectively, a dividing circuit responsive to the amplified first and second signals to produce a third electrical signal indicative of the ratio of said amplified signals, and a meter for displaying said third signal.

7. A sorter according to claim 6 wherein said meter provides a digital display of said third signal.

8. A sorter according to claim 7 including switching means and a timer, said switching means being effective to energize said timer in response to a predetermined displacement of both of said probes from their respective maximum protrusion positions, and said timer being connected to said meter and effective upon energizing thereof to provide sequentially an enabling signal to cause said meter to display an indication of said third signal and a holding signal to prevent any change in the displayed indication with changes in said third signal.

9. A sorter according to claim 8 wherein said enabling and holding signals are maintained throughout the period of energization of said timer and for a predetermined duration after de-energization of said timer unless said timer is re-energized prior to said duration.

* * * * *